(12) United States Patent
Kirkpatrick et al.

(10) Patent No.: US 8,562,600 B2
(45) Date of Patent: Oct. 22, 2013

(54) INTEGRATION OF CONTROL SOFTWARE WITH A MEDICAL DEVICE AND SYSTEM

(75) Inventors: Bruce E. Kirkpatrick, Santa Clara, CA (US); Timothy E. Ciciarelli, San Jose, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1447 days.

(21) Appl. No.: 11/964,946

(22) Filed: Dec. 27, 2007

(65) Prior Publication Data
US 2009/0171202 A1    Jul. 2, 2009

(51) Int. Cl.
*A61B 18/00* (2006.01)

(52) U.S. Cl.
USPC .......................................................... 606/34

(58) Field of Classification Search
USPC ........................................ 606/27, 31, 34, 41
See application file for complete search history.

(56) References Cited

U.S. PATENT DOCUMENTS

| | | | |
|---|---|---|---|
| 5,383,874 A | | 1/1995 | Jackson et al. |
| 5,400,267 A | * | 3/1995 | Denen et al. ................. 702/59 |
| 5,651,780 A | | 7/1997 | Jackson et al. |
| 5,954,717 A | * | 9/1999 | Behl et al. .................... 606/34 |
| 5,997,528 A | * | 12/1999 | Bisch et al. ..................... 606/1 |
| 6,165,169 A | | 12/2000 | Panescu et al. |
| 6,611,793 B1 | | 8/2003 | Burnside et al. |
| 2004/0254569 A1 | * | 12/2004 | Brosch et al. ................ 606/27 |
| 2005/0203504 A1 | * | 9/2005 | Wham et al. ................. 606/34 |
| 2005/0288662 A1 | * | 12/2005 | Uchida et al. ................ 606/34 |
| 2006/0030904 A1 | | 2/2006 | Quiles |
| 2006/0079883 A1 | | 4/2006 | Elmouelhi et al. |
| 2006/0282071 A1 | | 12/2006 | Utley et al. |
| 2007/0167941 A1 | * | 7/2007 | Hamel et al. ................. 606/34 |
| 2007/0255276 A1 | | 11/2007 | Sliwa et al. |

FOREIGN PATENT DOCUMENTS

WO    WO-94/10922    5/1994

OTHER PUBLICATIONS

"Supplementary European Search Report", EP08868952.6-2305 Nov. 11, 2010.
International Searching Authority/US; International Search Report and Written Opinion for PCT/US08/84205, mailed Jan. 9, 2009.

* cited by examiner

*Primary Examiner* — Michael Peffley
*Assistant Examiner* — Daniel Fowler
(74) *Attorney, Agent, or Firm* — Dykema Gossett PLLC (57) ABSTRACT

A medical device for diagnosis or treatment of tissue is disclosed. The device includes an electronically-controlled tool configured for diagnosis or treatment, an electrical connector, and a computer readable memory. The electrical connector is configured for connection with an electronic control unit and configured to receive control signals, including signals concerning the operation of the tool, from the electronic control unit. The computer readable memory is accessible through the connector. The memory can include a set of programming instructions for control of the tool, and the programming instructions can be configured to be downloadable from the memory upon connection of the electrical connector with the electronic control unit. A system is also disclosed in which the electronic control unit is configured to transmit a data log from memory in the electronic control unit to the memory in the medical device upon the occurrence or detection of a predetermined event.

24 Claims, 5 Drawing Sheets

INTEGRATION OF CONTROL SOFTWARE WITH A MEDICAL DEVICE AND SYSTEM

BACKGROUND OF THE INVENTION a. Field of the Invention

The invention relates to a system and method used for the diagnosis and/or treatment of tissue. More particularly, the instant invention relates to a system and method involving the integration of control software with a medical device that is configured for performing the diagnosis or treatment.

b. Background Art

Medical systems and procedures commonly involve the diagnosis and treatment of tissue. Conventional medical systems and procedures often involve the application of energy or electrical stimulus to tissue, for example, in surgical ablation procedures associated with endocardial and epicardial applications. An example of such a procedure is epicardial ablation for creating a transmural lesion. Other systems and procedures also may involve various mapping, diagnosis, and/or therapeutic functions or treatments.

Such medical systems and procedures commonly involve both reusable capital equipment and single-use, disposable devices. Moreover, the medical devices associated with such systems often include electronically-controlled tools (e.g., ablation catheters, probes, electrodes, or transducers), which may be software controlled.

Some conventional software-controlled medical systems and devices include a non-volatile storage memory (e.g., EPROM) that provide identification and/or calibration data or information to various types of control units. However, for many applications it may be desirable to provide a medical device or tool that can offer additional benefits) and that, at least to some extent, can be characterized as a "smart" medical device.

Additionally, when a fault is associated with conventional disposable devices, such devices are commonly returned with just the instrument's identification information, such as serial numbers, type of device, or other identification "tags," embedded therein. Engineers and technicians typically request and obtain logs from the associated capital equipment. Such logs are typically uploaded or transferred to some form of media and are separately provided for analysis. It is therefore desirable for devices and/or procedures that simplify or otherwise improve the fault-reporting process.

BRIEF SUMMARY OF THE INVENTION

The invention relates to a device and system that may be employed for diagnostic and/or therapeutic procedures in medicine, including minimally invasive cardiac electrophysiology studies and/or cardiac ablation procedures. The device includes an electronically-controlled tool configured for diagnosis or treatment, an electrical connector, and a computer readable memory. The electrical connector is configured for connection with an electronic control unit and configured to receive control signals, including signals concerning the operation of the tool, from the electronic control unit.

The computer readable memory is accessible through the connector. The memory can include a set of programming instructions for control of the tool, and the programming instructions can be configured to be downloadable from the memory upon connection of the electrical connector with the electronic control unit.

A system is also disclosed in which the electronic control unit is configured to transmit a data log from memory in the electronic control unit to the memory in the medical device upon the occurrence or detection of a predetermined (i.e., a select or predetermined) event.

The foregoing and other aspects, features, details, utilities and advantages of the present invention will be apparent from reading the following description and claims, and from reviewing the accompanying drawings.

DETAILED DESCRIPTION OF EMBODIMENTS OF THE INVENTION

Figure 1:
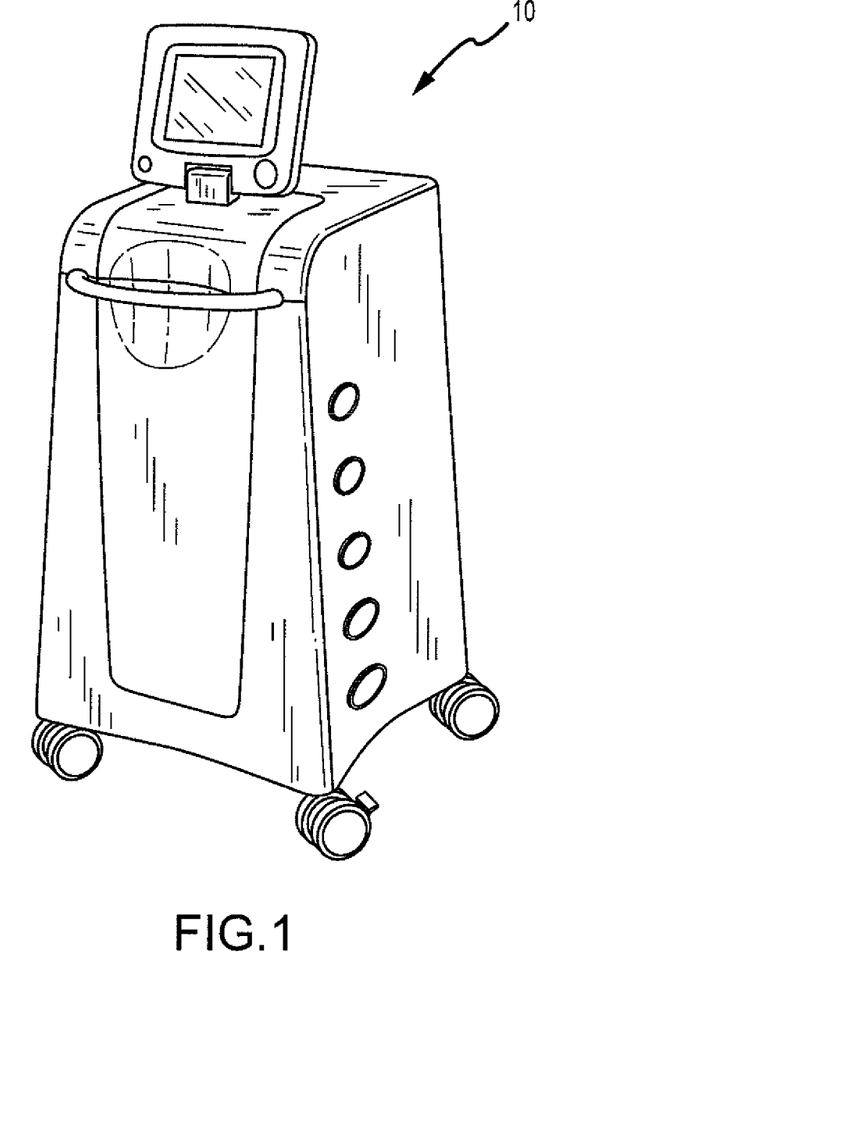
FIG. 1 is a graphical perspective representation of a control unit in accordance with an embodiment of the invention.
Figure 2:
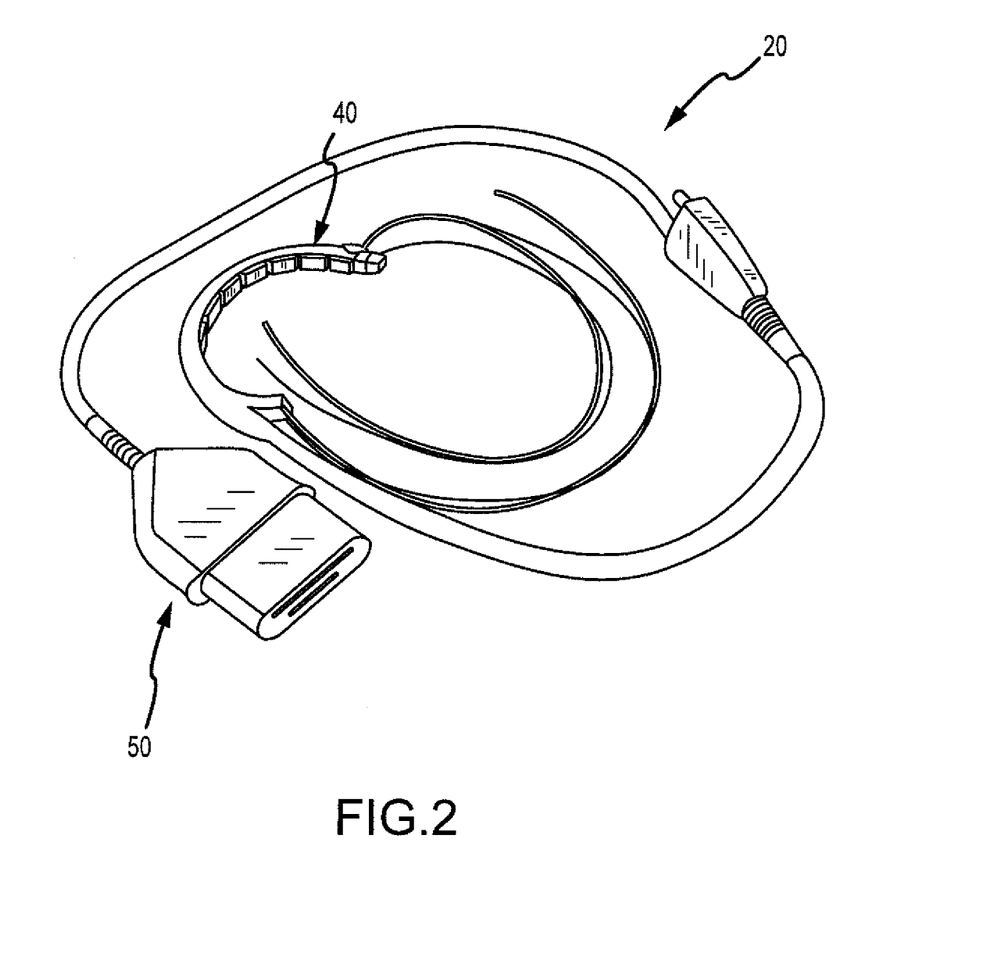
FIG. 2 is a graphical perspective representation of a medical device in accordance with an embodiment of the invention.
Figure 3:
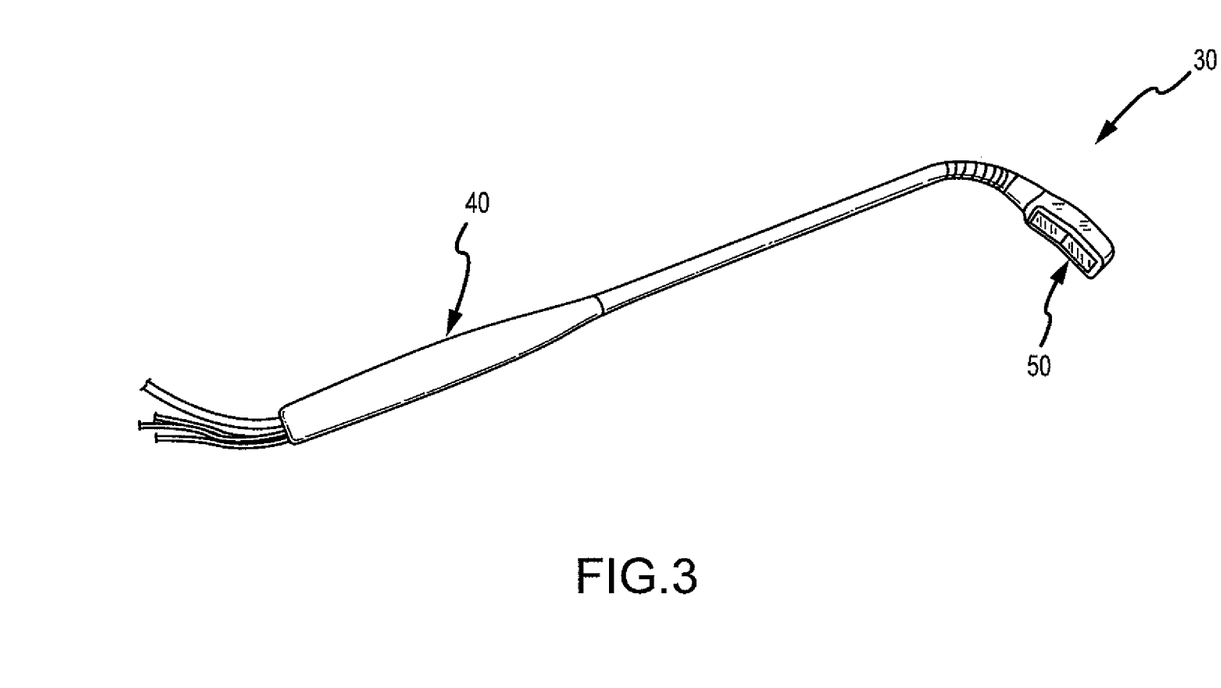
FIG. 3 is a graphical perspective representation of a medical device in accordance with an embodiment of the invention.

Referring now to the drawings wherein like reference numerals are used to identify identical components, FIG. 1 generally illustrates a perspective view of an electronic control unit 10 in accordance with an embodiment of the invention. FIGS. 2 and 3 generally illustrate exemplary medical devices 20, 30 that may be used in connection with various types of electronic control units in connection with the diagnosis and/or treatment of tissue. Together an electronic control unit (e.g., control unit 10) and an associated medical device (e.g., devices 20 or 30) may be combined to form a medical "system." However, the invention is not limited to the exemplary control unit and medical devices illustrated, and numerous other electronic control units, medical devices, and associated systems may come within the spirit and scope of the inventive concept.

In accordance with an embodiment of the invention, an electronic control unit, which may also be referred to as an "ECU" or an "electronic control system," includes a memory, such as an internal resident memory. The electronic control unit can be adapted or configured for connection with one or more medical devices, and may further be configured to, among other things, provide control signals to a connected medical device. For some applications the electronic control units may provide or deliver energy, e.g., ablative energy, such as ultrasound or HIFU, and may include various user interface features and controls. An example of a control unit, without limitation, is the Epicor™ Ablation Control System (ACS) offered by St. Jude Medical.

The medical device comprises a device for the diagnosis or treatment of tissue. In embodiments of the invention, for example as generally illustrated in FIGS. 2 and 3, the medical device 20,30 includes an electronically-controlled tool 40, an electrical connector 50, and a computer readable memory.

The electronically-controlled tool 40 may be configured for diagnosis and/or therapeutic treatment of tissue. For example, the electronically-controlled tool may include an ablation device—e.g., an ablation catheter and/or one or more ultrasound transducers, which may include one or more high intensity focused ultrasound (HIFU) transducers. In an embodiment, the tool may be configured for performing cardiac ablation, such as epicardial ablation. However, the tool associated with the system may take the form of various other electronically-controlled tools, and is not limited to the exemplary tools 20, 30 shown in connection with FIGS. 2 and 3. Moreover, if desired, for a number of applications, the medical device can comprise a single-use or disposable medical device. Examples of medical devices that may be used in connection with embodiments of the invention include, without limitation, The UltraCinch™ Ablation Device and The UltraWand™ Handheld Ablation Device, both offered by St. Jude Medical.

The electrical connector 50 may be configured for connection with a compatible electronic control unit, and may further be configured to receive control signals from the electronic control unit. The computer readable memory associated with the medical device may be accessible through the electrical connector 50, and may include a set of programming instructions that, at least in part, are used to control the associated tool. If desired, the computer readable memory may be resident within a portion of the electrical connector and/or the electronically-controlled tool. Further, rather than just providing a static non-volatile memory, the computer readable memory associated with embodiments of the invention may instead be configured to provide a desired level of computing capability in connection with the medical device itself.

In an embodiment, the programming instructions associated with the computer readable memory can, among other things, comprise a transient computer script, code, module, or algorithm (the foregoing individually and collectively hereinafter simply referred to as "script") configured to control some aspect associated with the operation of the tool by the electronic control unit. By way of example, the programming instructions can be used to implement "control variations," such as those in the form of temporary software changes. As such, the medical device, which for a number of embodiments may be disposable, can provide data or instructions to the electronic control unit that may be application-specific, so as to better optimize use or one or more functions associated with the behavior of the system and/or the specific medical device or the associated tool at the point of care. For example, a medical device (e.g., an epicardial ablation device) with an improved or upgraded membrane that does not require constant fluid flow to mitigate risk of device damage during low-frequency ablation might alter the ECU programming instructions to disable or reduce fluid flow, thereby improving energy delivery to targeted tissue. Likewise, a medical device that requires more energy than the electronic control unit to which it is connected can deliver might, for instance, perform a calibration check and disallow therapy delivery. In other words, instead of the control unit rejecting or refusing to operate with a medical device, which may be based on older algorithms established when the control unit was manufactured, the medical device may refuse to work with or otherwise reject operation with the control unit.

In another embodiment, the programming instructions associated with the computer readable memory of the medical device can, among other things, permanently alter another set of programming instructions resident in the memory of the electronic control unit. If desired, the medical device may be disposable, and/or may perform software maintenance and/or software upgrades with respect to the electronic control unit. Value-added upgrades can be made in a visible manner (i.e., where a user/customer is cognizant that they are obtaining maintenance or an upgrade that may have been procured) or, if desired, in a substantially or even completely transparent manner with respect to a user. Consequently, to the extent desired, a "smart" medical device in accordance with aspects of the invention can be configured to, at least in part, serve as a means for providing a desired upgrade that can, as desired, be distributed to intended targets within the device supply chain. As a further example, medical devices in accordance with the invention may be used to improve localization of user interfaces. That is, many electronic control units are provided with multiple language software to assist with expanded, or even world-wide, distribution. With smart medical devices as taught herein, language data stored in the memory of the medical device can be specific to a location or targeted market or region. Such product specification may reduce the control unit's (and the overall system's) associated memory requirements, and may simplify access to new markets. Also, in cases where the medical device provides an associated upgrade, the chance that a wrong or unintended version of an upgrade will be implemented with respect to a specific electronic control unit, as compared to separate upgrades involving human-initiated upgrades, can be reduced.

In yet another embodiment, the programming instructions associated with the computer readable memory of the medical device can, among other things, include instructions involving a user interface, a safety-monitoring feature, and/or a parameter associated with ablation. Additionally, the computer readable memory may include a set of data that is downloadable from the memory upon connection of the electrical connector with the electronic control unit. The data that is downloadable can, for example, be used in connection with the calibration of the electronically-controlled tool.

Figure 4:
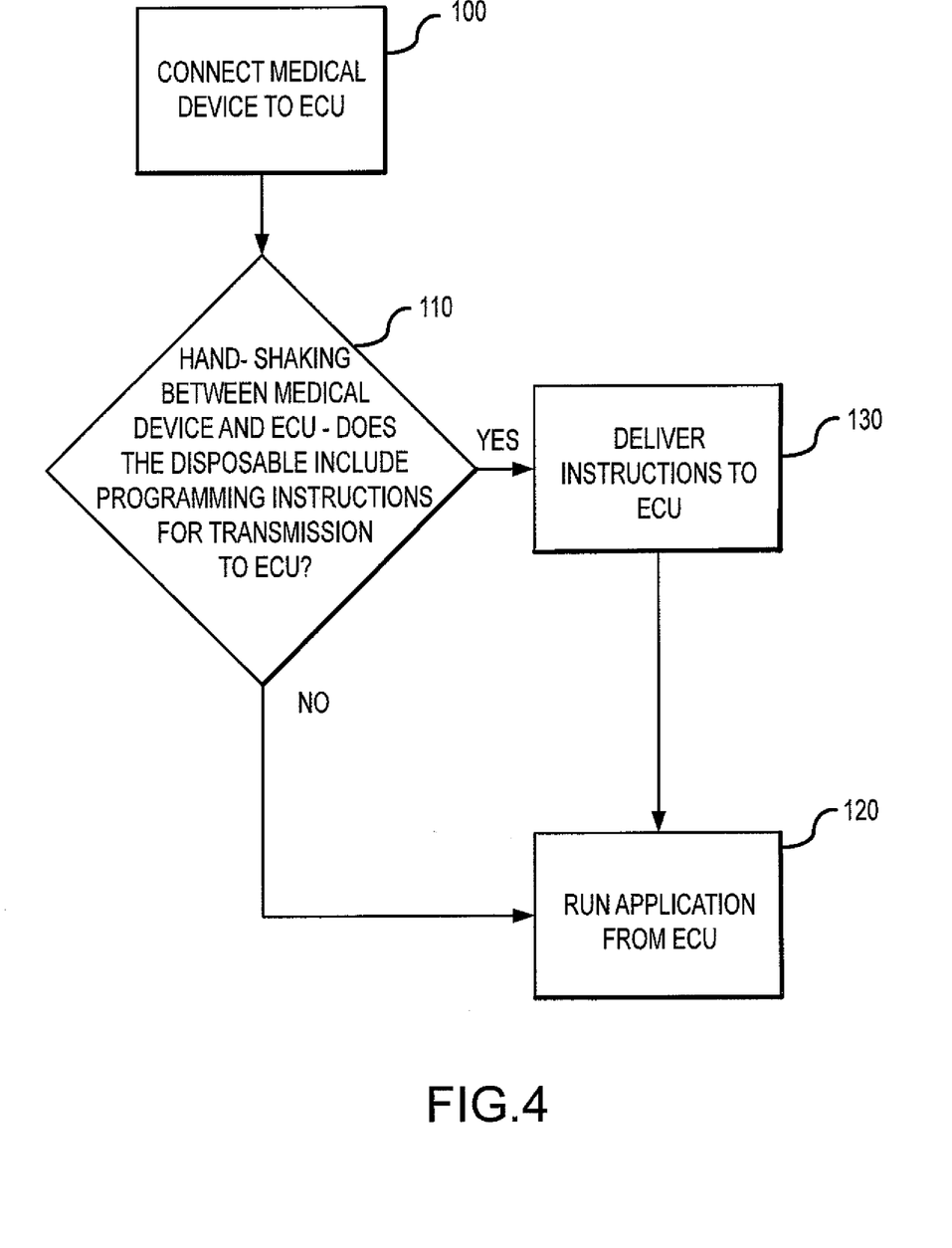
FIG. 4 is a flowchart generally depicting an exemplary method of providing programming instructions to an electronic control unit according to an embodiment of the invention.

FIG. 4 comprises a flowchart generally illustrating a method of providing programming instructions to an electronic control unit according to an embodiment of the invention. At step 100 a medical device is connected to an electronic control unit. In an embodiment, the electronic control unit can recognize the presence of a script and run or process all or a portion of the script (as perhaps directed by the script itself). At step 110, which occurs at some point after connection, a communication, or "handshaking," is performed between the medical device and the electronic control unit, and software associated with the ECU determines if the computer readable memory of the medical device includes programming instructions that are intended to be delivered to the electronic control unit. If the answer is no, the method continues with the running of the application, as generally noted at step 120. However, if instead it is determined that the medical device includes programming instructions for delivery to the ECU, the instructions are delivered to the ECU (e.g., step 130) as an intermediary step prior to the running of the application (step 120).

In connection with another embodiment of the invention, a system is disclosed in which an electronic control unit is configured for connection to a medical device and is further configured to transmit a data log from ECU memory (e.g., resident memory associated with the ECU) to memory (e.g., computer readable memory) associated with the connected medical device. The term "data log" is meant to be expansive with respect to the reporting of faults or errors associated with the system and may, among other things, include various forms and formats for reporting errors or faults, including various environmental and/or performance or operational event-related data or information. In some embodiments of the invention, the format associated with the data log may be specified or standardized. A system in accordance with such an embodiment may be configured so that a data log is transmitted upon or following the occurrence or detection of a predetermined event. Additionally, it is noted that such an embodiment may be further combined or used in connection with aspects of one or more of the previously-disclosed embodiments, including those involving various programming instructions.

As with previously-described embodiments of the invention, computer readable memory associated with the medical device may be provided as a sub-component within a tool or an electrical connector. Further, the predetermined event may include a fault (e.g., a system error or fault) detected by the electronic control unit. Examples of faults may include, without limitation, one or more of the following: a power delivery error, a temperature error, a pressure error, a hardware malfunction, or a software malfunction. The predetermined event may further include a user input to the electronic control unit.

The ECU may detect a fault, including those faults currently detected by conventional systems, for example, low cooling pressure. With conventional systems, the medical device is commonly returned to the manufacturer and the fault is typically reported to a quality technician or engineer who will want to obtain relevant information, including real-time data, such as the temperatures that were reached during operation. In connection with the investigation, the logs from the ECU will usually be requested and uploaded in some type of electronic form that generally must be filtered to hopefully find records that identify the cause of the fault or failure.

In contrast, the present invention may provide a device and related system in which the ECU may be configured, for example, to transmit or copy the recorded log in real-time when a fault condition (e.g., low pressure) is detected. Having the suspect medical device store relevant data in its memory to a device that is being returned for inspection and analysis before it is disconnected can provide an effective and convenient way to transfer all or portions of the relevant troubleshooting information, which conventionally would need to be separately downloaded and provided in some other media or form. Embodiments of the present invention can streamline such error or fault analysis by providing the device and necessary and/or relevant information and data altogether and at the same time, without requiring a site visit to the control unit, which is commonly much bulkier and may not need to be returned.

Figure 5:
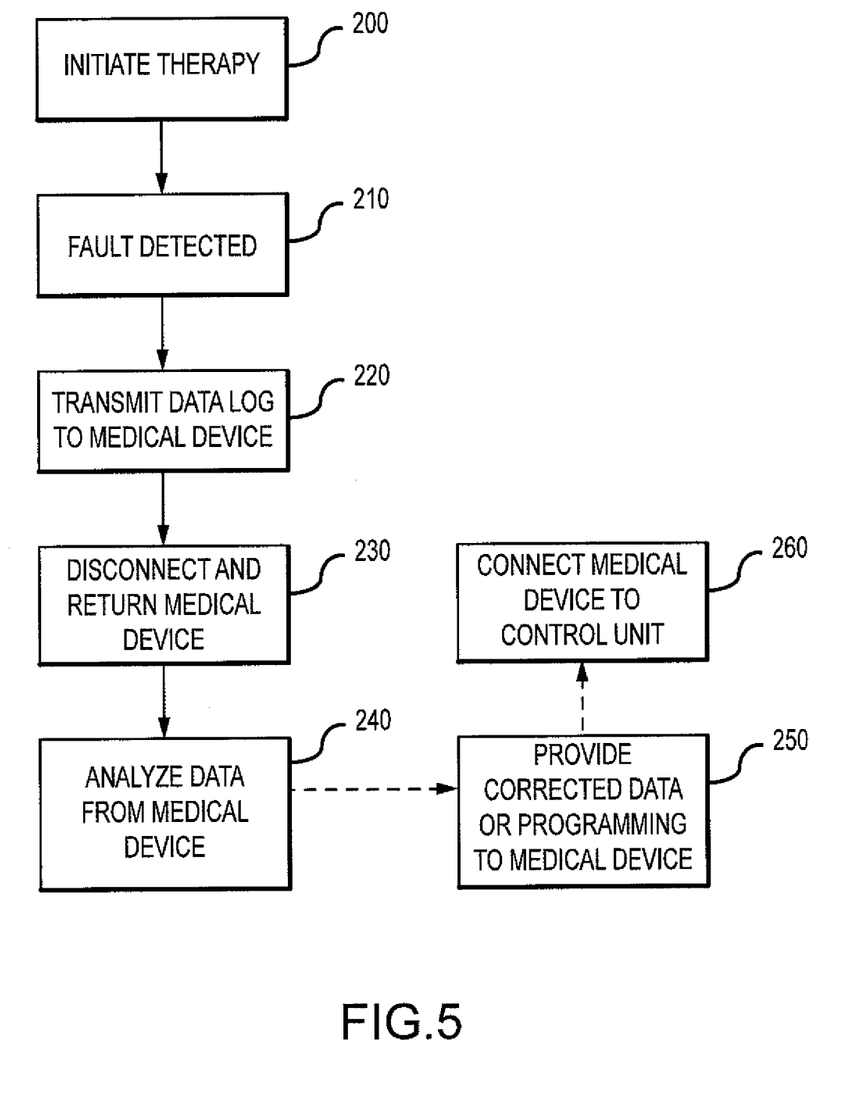
FIG. 5 is a flowchart generally depicting an exemplary method of providing data log information from a memory associated with a control unit to a memory associated with a disconnectable medical device according to an embodiment of the invention.

FIG. 5 comprises a flowchart generally depicting an exemplary method of providing data log information from a memory associated with a control unit to a memory associated with a disconnectable medical device according to an embodiment of the invention. At step 200, a therapy is initiated by the medical system. At some point, whether during calibration, initialization, or during activation, a fault is detected by the system—typically by the electronic control unit (step 210). The electronic control unit then, which may substantially be in real-time, transmits a data log to the computer readable memory associated with the associated medical device (step 220). Some time after the medical device receives and stores fault-related data (i.e., a data log) provided by the control unit, the entire medical device, or the portion of the device including the memory, can be disconnected from the control unit and returned to the manufacturer, or other appropriate party (step 230). The data log stored in the memory of the medical device can then be analyzed (step 240).

As further generally illustrated in FIG. 5, a method in accordance with the present invention can, optionally, also involve a step (e.g., step 250) of providing updated or corrected data or other programming to the medical device in question (if the device is capable of re-use) or to another (typically similar) medical device for transmission of corrected data or other programming (e.g., a script) to the associated control unit or, in some cases, to another compatible control unit. As generally noted in connection with step 260, an "updated" medical device can then, under appropriate conditions, be connected to the associated control unit or to a compatible unit to provide updated or corrective data or information to the unit.

In yet a further embodiment of the invention, even if no problematic fault is detected by the system, a user may intentionally initiate or otherwise provide for a different form of predetermined event or occurrence that is associated with the transfer all or portions of select or desired system data or information to the medical device. The transferred data and/or information, which may be stored in the computer readable memory of the medical device, can later be used in connection with further data analysis of the system and/or the device. Such information can be very useful for a variety of purposes. By way of example, without limitation, at times surgeons may make observations during a procedure, even to the extent of FDA reportable events, for which subsequent analysis may be required, and which would typically involve access and review of instrument data logs. Such user-initiated "recordings" may also help rule out certain contributing factors. Moreover, for pre-market clinical trial studies, study data could be returned from a trial site to a study coordinator on a per-case basis using systems and devices provided in accordance with aspects and embodiments of the invention. In yet a further exemplary embodiment, the system may be configured such that even if no fault is detected, the ECU may transparently initiate, or a user may intentionally schedule, set up or initiate, or otherwise provide a pre-determined event or occurrence for the transfer of data or other information to the medical device. For instance, the system may be configured to automatically provide a specified type or form of data log to the medical device at a scheduled time or following the conclusion of a treatment or therapy. Further, such transfers, may be substantially transparent to the user in the sense that the transfers may occur without requiring the user to take affirmative action or notice.

Although several embodiments of this invention have been described above with a certain degree of particularity, those skilled in the art could make numerous alterations to the disclose embodiments without departing from the spirit or scope of this invention. All directional references (e.g., upper, lower, upward, downward, left, right, leftward, rightward, top, bottom, above, below, vertical, horizontal, clockwise and counterclockwise) are only use for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the spirit of the invention as defined in the appended claims.

What is claimed is:

1. A medical device for diagnosis or treatment of tissue, comprising:

an electronically-controlled tool configured for diagnosis or treatment of tissue;

an electrical connector configured for removable connection and disconnection with an electronic control unit and configured to receive control signals from the electronic control unit, the control signals controlling operation of the tool; and a computer readable memory accessible through the connector, the memory including a set of programming instructions configured to control operation of the tool by the electronic control unit, the programming instructions downloadable from the memory upon connection with the electronic control unit, wherein the computer readable memory is provided as a sub-component within the electronically-controlled tool or the electrical connector, wherein the programming instructions provided on and by the medical device are configured to reprogram at least a portion of the programming instructions resident in a memory of the electronic control unit, and wherein the programming instructions provided on and by the medical device are configured to provide temporary software changes to at least a portion of the programming instructions resident in the memory of the electronic control unit that are application-specific to the medical device.

2. The device of claim 1, wherein the medical device comprises a single-use or disposable medical device.

3. The device of claim 1, wherein the tool comprises an ablation catheter.

4. The device of claim 1, wherein the tool comprises an epicardial cardiac ablation device.

5. The device of claim 1, wherein the tool comprises one or more ultrasound transducers.

6. The device of claim 5, wherein the tool comprises one or more high intensity focused ultrasound (HIFU) transducers.

7. The device of claim 1, wherein the memory further includes a set of data downloadable from the memory upon connection with the electronic control unit, the data configured for calibration of the tool.

8. The device of claim 1, wherein the programming instructions provided on and by the medical device permanently alter another set of programming instructions resident in a memory of the electronic control unit.

9. The device of claim 1, wherein the programming instructions include instructions involving a user interface, a safety-monitoring feature, or a parameter associated with ablation.

10. A medical system for diagnosis or treatment of tissue, comprising:

an electronic control unit; and a medical device including:

an electronically-controlled tool configured for diagnosis or treatment of the tissue;

an electrical connector configured for removable connection and disconnection with the electronic control unit and configured to receive control signals from the electronic control unit, the control signals controlling operation of the tool; and a computer readable memory accessible through the connector, the memory including a set of programming instructions configured to control operation of the tool by the electronic control unit, wherein the programming instructions provided on and by the medical device are configured to reprogram at least a portion of the programming instructions resident in a memory of the electronic control unit, and wherein the programming instructions provided on and by the medical device are configured to provide temporary software changes to at least a portion of the programming instructions resident in the memory of the electronic control unit that are application-specific to the medical device;

wherein the electronic control unit is configured to transmit a data log from a memory in the electronic control unit to the memory in the medical device upon or following the occurrence or detection of a predetermined event.

11. The system of claim 10, wherein the computer readable memory is provided as sub-component within the electronically-controlled tool or the electrical connector.

12. The system of claim 10 wherein the predetermined event comprises detection of a system fault by the electronic control unit.

13. The system of claim 12, wherein the system fault comprises one or more of the following: a power delivery error, a temperature error, a pressure error, a hardware malfunction, or a software malfunction.

14. The system of claim 10, wherein the predetermined event includes a user input to the electronic control unit.

15. The system of claim 10, wherein the medical device comprises a single-use or disposable medical device.

16. The system of claim 10, wherein the tool comprises an ablation catheter.

17. The system of claim 10, wherein the tool comprises an epicardial cardiac ablation device.

18. The system of claim 10, wherein the tool comprises one or more ultrasound transducers.

19. The system of claim 18, wherein the tool comprises one or more high intensity focused ultrasound (HIFU) transducers.

20. The system of claim 10, wherein the memory of the medical device further includes a set of data downloadable from the memory of the medical device upon connection with the electronic control unit, the data configured for calibration of the tool.

21. The system of claim 10, wherein the memory of the medical device includes a set of programming instructions for control of the tool, the programming instructions downloadable from the memory of the medical device upon connection with the electronic control unit.

22. The system of claim 21, wherein the programming instructions comprise a transient script configured to control operation of the tool by the electronic control unit.

23. The system of claim 21, wherein the programming instructions permanently alter another set of programming instructions resident in the memory of the electronic control unit.

24. An electronically-controlled tool configured for connection to an electronic control unit and configured for diagnosis or treatment of tissue, the tool comprising:

an electrical connector configured for connection with said electronic control unit and configured to receive control signals from said electronic control unit, the control signals controlling operation of the tool; and a computer readable memory accessible through the connector, the memory including memory for storing a set of programming instructions configured to control operation of the tool by the electronic control unit and memory for storing a data log transmitted by said control unit upon or following the occurrence or detection of a predetermined event;

wherein the programming instructions are downloadable from the memory upon connection with the electronic control unit and wherein the programming instructions provided on and by the medical device are configured to reprogram at least a portion of the programming instructions resident in a memory of the electronic control unit, and wherein the programming instructions provided on and by the medical device are configured to provide temporary software changes to at least a portion of the programming instructions resident in the memory of the electronic control unit that are application-specific to the medical device.

* * * * *